United States Patent
Gamache et al.

(10) Patent No.: US 6,637,277 B2
(45) Date of Patent: Oct. 28, 2003

(54) FLUID SAMPLING DEVICE

(75) Inventors: Yves Gamache, St-Daniel (CA); André Fortier, St-Daniel (CA)

(73) Assignee: Contrôle Analytique Inc., Thetford Mines (CA)

( * ) Notice: Subject to any disclaimer, the term of this patent is extended or adjusted under 35 U.S.C. 154(b) by 17 days.

(21) Appl. No.: 09/805,698

(22) Filed: Mar. 13, 2001

(65) Prior Publication Data

US 2002/0129668 A1 Sep. 19, 2002

(51) Int. Cl.$^7$ ................................................ G01N 1/16
(52) U.S. Cl. ........................ 73/863.33; 73/864.85; 73/864.81
(58) Field of Search .................... 73/863.31, 863.33, 73/863.86, 863.71, 864.85, 864.81; 137/625.4, 606; 251/129.11

(56) References Cited

U.S. PATENT DOCUMENTS

| | | | |
|---|---|---|---|
| 4,090,392 A | * 5/1978 | Smith et al. | 73/863.33 |
| 4,800,763 A | * 1/1989 | Hakkers et al. | 73/863.31 |
| 5,054,309 A | 10/1991 | Mettes et al. | 73/1 G |
| 5,055,260 A | 10/1991 | Roberge et al. | 422/62 |
| 5,065,794 A | 11/1991 | Cheung | 137/883 |
| 5,239,856 A | 8/1993 | Mettes et al. | 73/1 G |
| 5,259,233 A | 11/1993 | Brandt | 73/1 G |
| 5,447,053 A | 9/1995 | Ohmi | 73/31.03 |
| 5,469,751 A | * 11/1995 | Weiss et al. | 73/863.33 |
| 5,587,519 A | 12/1996 | Ronge et al. | 73/1 G |
| 5,661,225 A | 8/1997 | Ridgeway et al. | 73/1.06 |
| 5,922,286 A | 7/1999 | Girard et al. | 422/83 |

FOREIGN PATENT DOCUMENTS

| JP | 85352 | * 5/1985 | 73/863.33 |
|---|---|---|---|

* cited by examiner

*Primary Examiner*—Daniel S. Larkin
*Assistant Examiner*—Nashmiya Fayyaz
(74) *Attorney, Agent, or Firm*—Darby & Darby

(57) ABSTRACT

A fluid sampling device or system for providing a fluid to a fluid processing apparatus. The system includes a plurality of sampling lines, each having an inlet line and an outlet line connected by a valve. The valve has a closed position preventing a fluid flow between the two lines and an opened position allowing such a fluid flow. A first and a second purge line are provided, respectively connected to the inlet and outlet lines for purging fluid therefrom. Rotameters or other similar devices are provided for controlling each of the purge lines. A connecting line is provided for connecting each of the outlet lines to each other and to the outlet. In operation, one of the valves is opened and the others are closed. Fluid flows from the selected valve to the apparatus and backwards through the outlet lines of the unselected sampling channels, providing a backpurge of these outlet lines through the second purge lines.

10 Claims, 6 Drawing Sheets

FLUID SAMPLING DEVICE

FIELD OF THE INVENTION

The present invention relates to the field of fluid sampling and concerns a sampling device or system particularly adapted for use in a gas analysis process.

BACKGROUND OF THE INVENTION

In all fields using a gas medium such as air separation processes, petroleum refining, natural gas production, semiconductor devices manufacturing, specialty gas laboratories, etc. all gas being processed or used in one way or another must be analyzed for quality control or process control. To perform such an analysis, a gas sample is collected and brought to an analytical measuring system. Generally, the gas sample is conveyed through metal tubing, up to a sample panel. A plurality of samples may need to be successively collected, depending on the complexity of a particular system. The analyzed sample should of course be representative of the gas medium being controlled.

The industry has used and still uses various devices and processes to bring a sample to an analytical system. With these sampling systems, contamination of a sample often occurs by mixing it with previously selected samples, leaks in or out of the sampling system or leaky valves.

FIG. 1 (prior art) illustrates a sampling process frequently used in older systems and is still in use today. In this system 10, various sample lines 12 made of various tubing material each bring a corresponding sample to the apparatus sample inlet 14. A plurality of sampling locations may be provided, as required by the process to be monitored. A bypass rotometer 16 is provided in each line, for purging a given sampling line 12 when not selected. The rotometer 16 allows fixing of a bypass flow and preferably sets a high flow in the sample line 12 to speed up the purge time. The excess flow is vented out of the system. A female quick connector 18 is provided at the extremity of each sampling line 12 and is adapted to receive a male quick connector 20 allowing the sample to flow through the flexible line 22 up to the analytical system 24. To change the selected sample line 12, the male quick connector 20 needs to be removed from the female quick connector 18 and inserted in another one. This system makes sure that there is no sample cross contamination from various sample points, since the sampling lines 12 are physically isolated. However, this system has serious drawbacks. First, each time the male quick connector 20 is disconnected from a female quick connector 18, the gas flow to the analytical system 24 is momentarily interrupted. Some analytical systems 24 are affected by the sample flow variation. Also the female and male quick connectors 18 and 20 have some internal dead volume that will be filled with atmospheric air when disconnected from each other. This air is directed to the analytical system and serious pollution may occur when measuring $H_2O$, $O_2$ or $N_2$ as impurities in a particular background. Another drawback is that the quick connectors 18 and 20 tend to wear out with use, resulting in leaks leading to wrong analytical results. Another problem with this system is related to the use of flexible tubing. Often this tube is made of various plastic or polymers that exhibit too much permeation to $O_2$ and $H_2O$ polluting the sample. When flexible metal tubing is used, it must be replaced often since metal fatigue due to manipulation causes them to break.

FIG. 2 (prior art) shows another sample stream selection used in the industry. This system 10 is similar to the one of FIG. 1, but uses instead of quick connectors, a rotary selection valve 26 well known in the industry and available from various manufacturers. This system 10 alleviates some of the drawbacks of the previous one, but introduces cross port flow contamination that increases with time. If a sample line 12 has a higher pressure, it will leak through the valve body 26 and pollute the stream being measured. This valve requires frequent replacement. Furthermore, leaks can occur from the valve stem.

FIG. 3 (prior art) shows another system used in the industry. In this system 10 each sampling line 12 includes an ON/OFF valve 28 provided downstream the bypass rotometer 16. However, this system introduces dead volume in the line section 30 downstream the valve 28. When switching from one sample to a new one, the line section of the previously selected sample is full of the previous sample. This gas is trapped there and will slowly diffuse in the line, slowing down the response time of the system and causing drifting readings of the analytical system 24. Another source of unswept dead volume is the valve itself. The space surrounding the valves plunger is always filled with sample gas and slowly diffuses in the main stream, causing measurement drift and noise. A Diaphragm based valve may be used to reduce the problem, but it increases the cost of the system since most of the time the use of such a valve will involve orbital welding for assembly. Furthermore, over time, ON/OFF valves will develop leaks. So an unselected stream may leak to a selected one, resulting in analytical error measurement and apparent drift or noise when the sample line pressure varies again. As soon as a valve develops a leak it must be replaced, interrupting the system in service. There are some variations of the previously described systems but all have similar drawbacks.

Also known in the art is U.S. Pat. No. 5,922,286 (GIRARD et al). Girard discloses a system that selects individual sample streams with the help of a 4-way, pneumatic actuated, VCR ¼" connected diaphragm valve. Even if this system succeeds in eliminating unswept volume present on the discharge side of the valve and provides some means to have a sample inlet bypass flow or purge, it fails to eliminate the problem associated with leaking valves, i.e. crossport flow contamination. The selected sample must flow through all unselected valve bodies just around the seat, which is quite large. Therefore, the risk of crossport contamination increases with the number of sampling lines in the system. Diaphragms having a relatively short useful life there will eventually be leaking across the seat and contamination of the selected sample. Finally the diaphragm valves used in this system are costly and the total space required for this system is quite large.

Other related prior art systems include U.S. Pat. Nos. 5,054,309; 5,055,260; 5,065,794; 5,239,856; 5,259,233; 5,447,053; 5,587,519 and 5,661,225.

OBJECTS AND SUMMARY OF THE INVENTION

It is an object of the present invention to provide a fluid sampling system that prevents cross-port flow contamination between various sampling lines.

It is another object of the invention to provide such a system that may be manufactured inexpensively.

It is a preferable object of the present invention to provide such a system that is insensitive to valve leaks.

It is also a preferable object of the invention to provide such a system allowing an evacuation of dead volume from the valves used.

The present invention therefore provides a fluid sampling system for providing a fluid sample to a fluid processing apparatus. The sampling system has a sample outlet connected to said apparatus, and a plurality of sampling channels. Each of the sampling channels includes the following elements:

an inlet line receiving a fluid and an outlet line conveying the fluid to the sample outlet;

a valve connected to the inlet line and to the outlet line, the valve having a closed position preventing a fluid flow between the inlet line and the outlet line and an open position allowing a fluid flow between the inlet line and the outlet line;

a first purge line connected to the inlet line and purging fluid therefrom, and a second purge line connected to the outlet line and purging fluid therefrom; and flow controlling means for controlling a fluid flow in the first and second purge lines.

The fluid sampling system further includes a connecting line for connecting the outlet lines of the sampling channels to each other and to the sample outlet, and valve control means for selectively setting the valve of one of the sampling channels in the opened position and the valves of the remaining sampling channels in the closed position.

Other features and advantages of the present invention will be better understood upon reading the following description of preferred embodiments thereof with reference to the appended drawings.

DESCRIPTION OF PREFERRED EMBODIMENTS OF THE INVENTION

Figure 4:
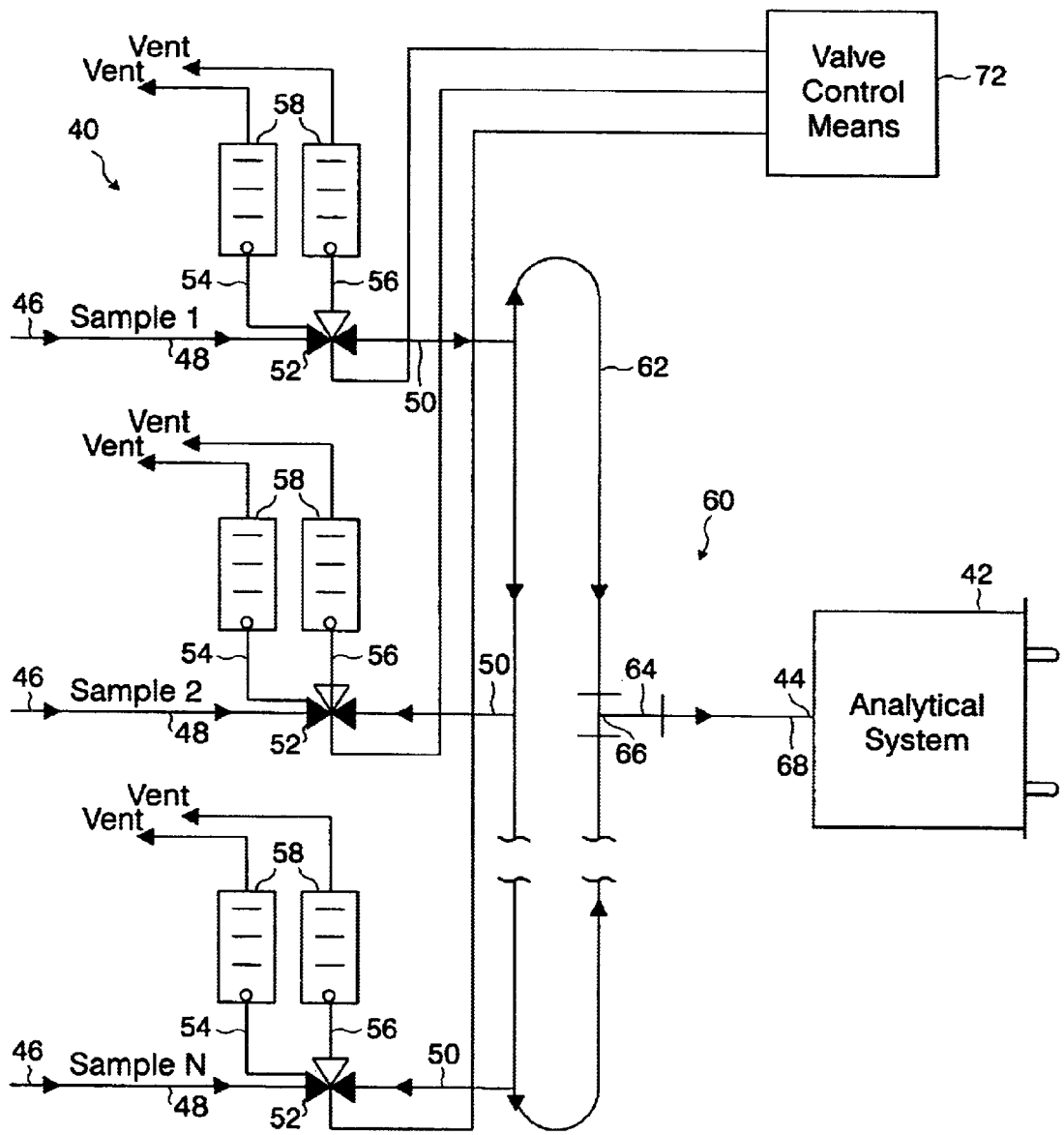
FIG. 4 is a schematic representation of a fluid sampling system according to a first embodiment of the invention.

Referring to FIG. 4, there is shown a system 40 according to a first preferred embodiment of the invention. The system provides a fluid sample to at least one fluid processing apparatus, here embodied by analytical system 42. It is however understood that the present system may for example alternatively be used to feed a process using fluid samples, or any other type or number of apparatus adapted to receive a fluid from a given medium. Also, in the illustrated embodiments the fluid sample is of the gaseous type, but the present invention may just as well be used to sample a liquid medium.

Figure 5:
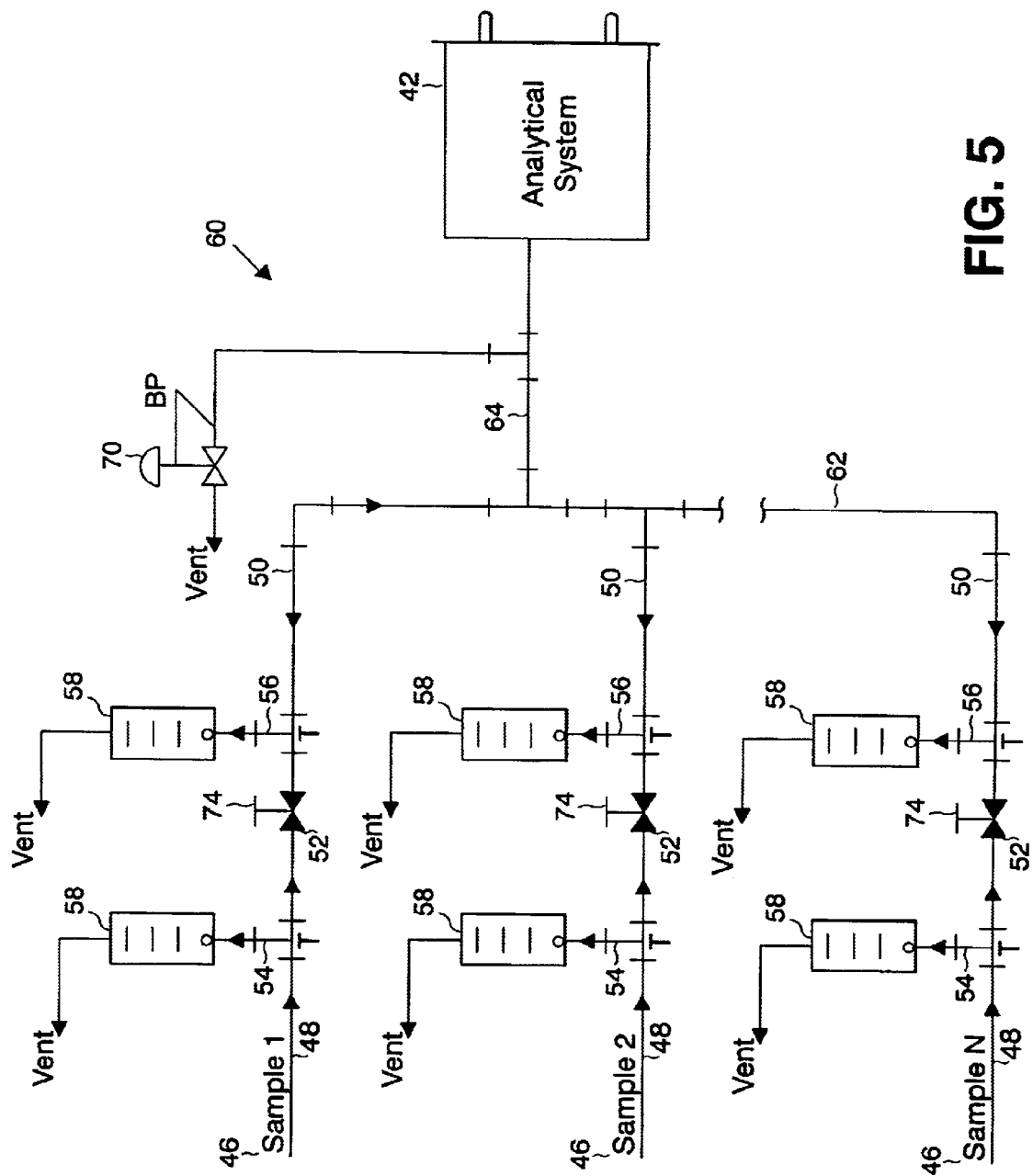
FIG. 5 is a schematic representation of a fluid sampling system according to a second embodiment of the invention.

The system 40 includes a plurality of sampling channels 46. In FIGS. 4 and 5, only three sampling channels are illustrated, but it is of course understood that as many channels as needed may be provided. Each channel has an inlet line 48 receiving the fluid from the medium to be sampled, and an outlet line 50 conveying this fluid to a sample outlet 44, connected to the apparatus 42. A valve connects the inlet line 48 to the outlet line 50. Each sampling channel 46 also includes a first purge line 54 connected to the inlet line 48, and a second purge line 56 connected to the outlet line 50.

Figure 1:
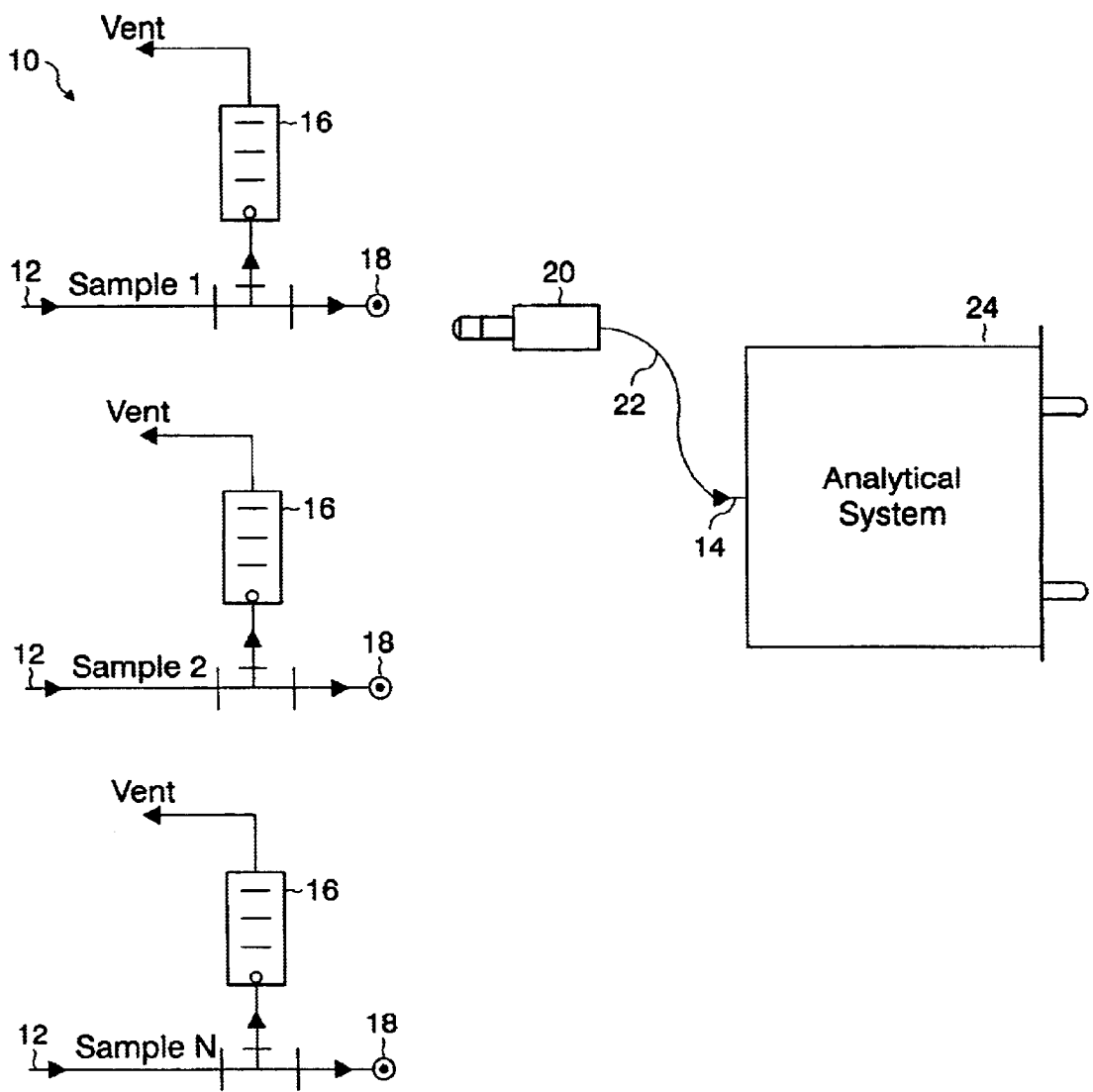
FIG. 1 (prior art) is a schematic representation of a first fluid sampling system known in the art.
Figure 2:
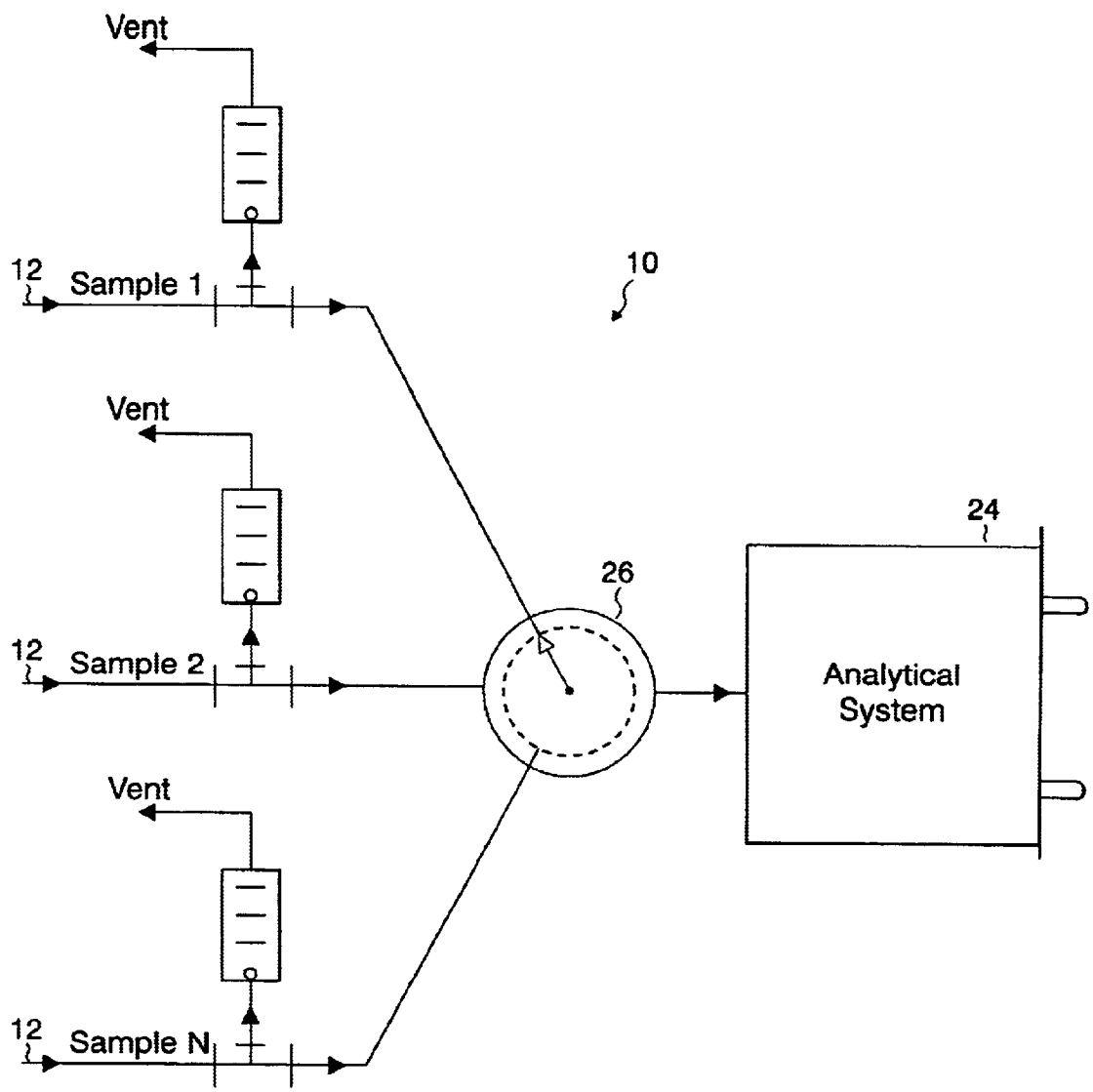
FIG. 2 (prior art) is a schematic representation of a second fluid sampling system known in the art.
Figure 3:
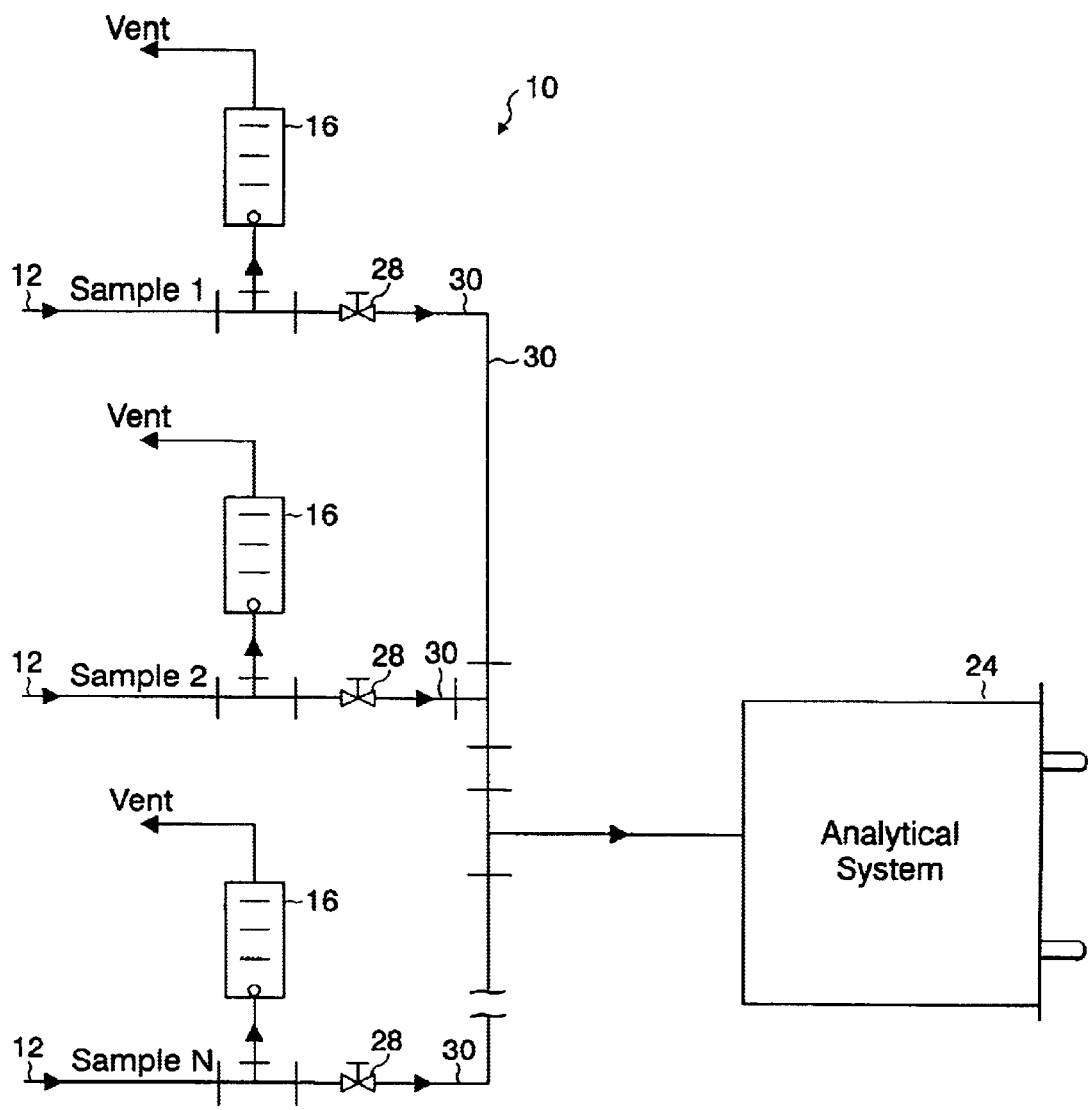
FIG. 3 (prior art) is a schematic representation of a third fluid sampling system known in the art.

When the valve 52 is in a closed position, it prevents a fluid flow between the inlet line 48 and outlet line 50. When opened, it allows such a fluid flow, effectively selecting the corresponding sampling channel for analysis. As with the prior art model shown in FIG. 3, the first purge line 54 purges fluid from the inlet line 48. The second purge line 56 purges fluid from the outlet line 50. Its function will be better explained later.

Each sampling channel 46 also includes flow controlling means, here embodied by standard rotometers 58 ("falling ball" flowmeters), for controlling the fluid flow in the first and second purge lines 54 and 56. In this manner, the fluid flow in each of the inlet and outlet lines is also adjusted as needed. Any other devices allowing to visualize and adjust fluid flow may alternatively be used, such as for example electronic flow sensors and electronic proportional valves connected to a microprocessor based system.

The system 40 further includes a connecting line 60 connecting the outlet lines 50 of the sampling channels 46 to each other and to the sample outlet 44. Preferably, the connecting line 60 has a first segment 62 connected to the sampling channel's outlet lines 50, and a second segment 64 having one end 66 connected to the first segment 62 and another end 68 connected to the sample outlet 44. The first segment may form a loop, as shown in FIG. 4.

To select a sample from a particular sampling line for analysis, the corresponding valve 52 must be opened while the others are closed. For example, in FIG. 4, the valve of sampling channel 1 is open, while sampling channels 2 and N are closed. For this purpose valve control means are provided, allowing to selectively opening the valve 52 of one of the sampling channels 46 and closing the valves 52 of the remaining sampling channels. These control means may include a manual actuator 74 provided on each valve 52 as shown in FIG. 5, or an electrical actuator 72 as shown in FIG. 4. The valves 52 may also be pneumatically actuated. It is understood that any appropriate means of controlling a valve may be used in the present system without departing from the scope of the invention.

With particular reference to FIG. 4, the operation of this illustrated embodiment of the invention will now be explained in more detail. The arrows on FIG. 4 indicate the gas flow paths in the system. In the present case, the sample valve 52 of sampling channel 1 is open, allowing a fluid flow therethrough. The fluid sample coming out of this valve flows through the corresponding outlet line 50, sweeps the looped first segment 62 in both direction and is then directed to second segment 64 up to the sample outlet 44 and the analytical system 42 where the sample is analyzed. The role of the loop in the first segment 62 is to allow an equal purging time for any of the selected sample channels.

Incoming fluid in the inlet line of the unselected channels is vented out of the system through the fist purge line 54. This "bypass" purge line is preferably located as close as possible to the valve seat. For this purpose, the inlet line 48 may pass through the valve body or, if valves are manifold mounted, it may be welded on the manifold just under valve seat. This provision advantageously allows the inlet portion of the valve body to be swept at all time by the sample fluid. The first purge line rotometer may be adjusted to set the bypass flow to the proper valve, in accordance with the length and pressure of the sample channel.

The outlet lines 50 of the unselected sampling channels 2 and N are backflushed with the fluid coming out of the selected sampling line 1. This has the effect of purging out the system, through second purge line 56, any sample previously selected, virtually eliminating the dead volume effect caused by the outlet lines of the sampling channels in previous systems.

Figure 6:
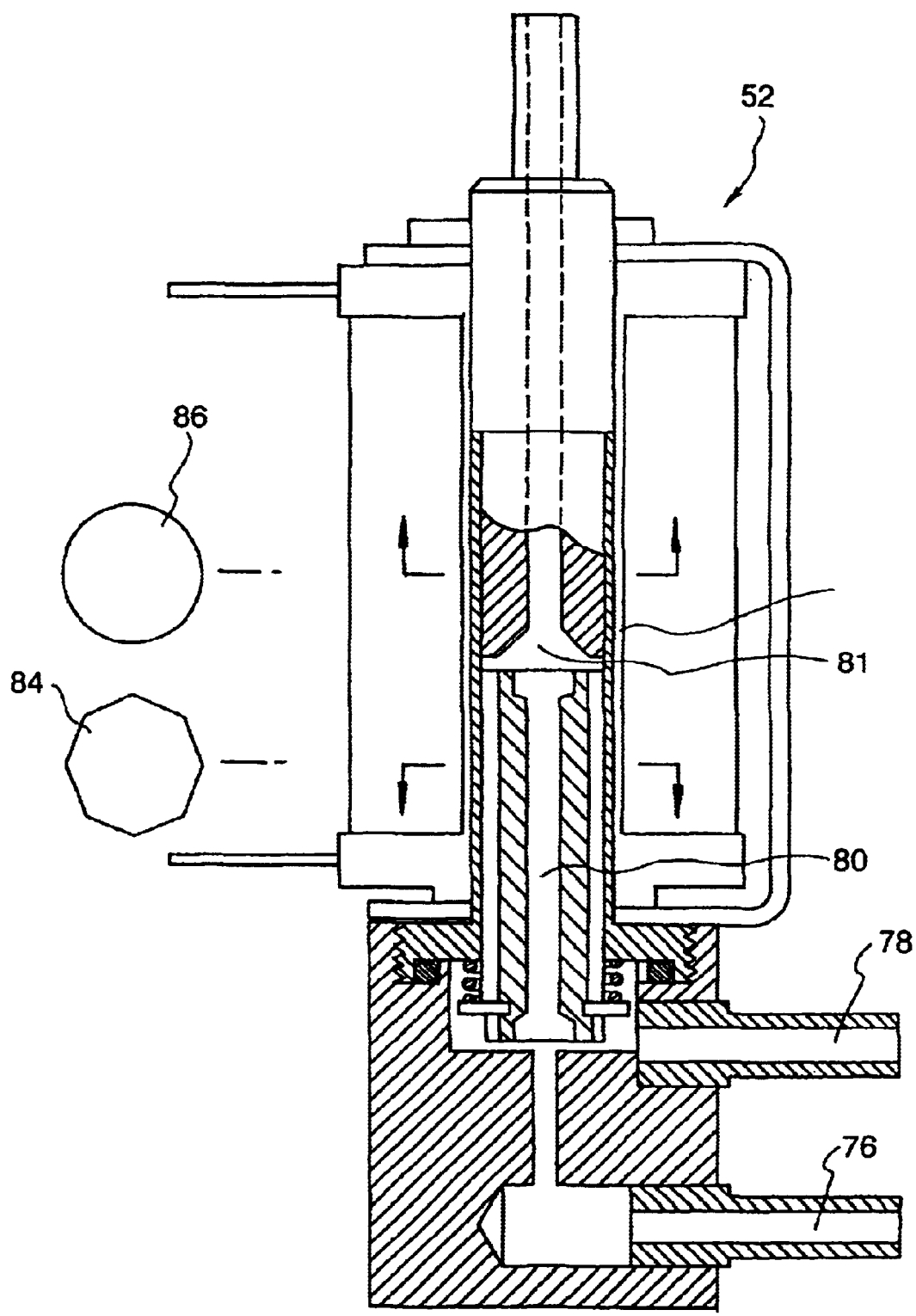
FIG. 6 is a side elevation view in transparency of a valve adapted for use in the embodiment of FIG. 4.

Preferably, the second purge line of each sampling channel is connected to the outlet line of the corresponding sampling channel through the corresponding valve, so that it may purge dead volume from the valve body. A valve model particularly adapted to such an embodiment is shown in FIG. 6. The valve 52 includes an inlet conduit 76 connected to the inlet line, and an outlet conduit 78 connected both to the outlet line and to the inlet conduit 76. A plunger 80 is translationally mounted in stem 81, for selectively blocking a flow of fluid between the inlet and outlet conduits 76 and 78. A purge conduit 81, defining the stem of the valve, is also provided and is connected to the second purge line and to the outlet conduit 78. The plunger 80 has a lower position where it blocks fluid flow from the inlet conduit 76, therefore closing the valve 52 as explained above. When the plunger 80 is in an upper position, fluid is allowed to flow from the inlet conduit 76 to the outlet conduit 78, defining the open position of the valve 52.

In this embodiment, the backpurge fluid flow is brought to the second purge line through the stem 81 of the valve. This feature of the invention is advantageous in that dead volume in the valve itself is also evacuated. Even more advantageously, the plunger 80 preferably has an octagonal cross-section 84, whereas the opening 82 has a circular cross-section 86, providing a backpurge of the valve stem 81 even when the valve 52 is open. In this manner, even when a given sampling line is selected the dead volume in its stem 81 is pushed in the second purge line and vented out of the system. Preferably, the second purge line rotometer is set to purge many times per minute the dead volume in both the valve stem and the outlet line. A typical flow value for example ranges from 20 to 50 cc/min.

Referring to FIG. 5, there is shown a second embodiment of the invention where the valves 52 are standard ON/OFF valves and the first and second purge lines are connected through discreet "T" fittings. In this embodiment, the first segment 62 of the connecting line 60 is not looped but simply has various connecting points to the sampling channels 42.

As shown in FIG. 5, a back pressure regulator 70 may be added in connection to the second segment 64 of the connecting line to maintain delivery pressure constant. As mentioned, the valves could be manually, pneumatically or electrically actuated. The various rotometers can also be replaced by electronic flow sensors and electronic proportional valves and connected to a microprocessor based system. All the systems can also be mounted in a purged enclosure eliminating any inboard contamination or making it usable in hazardous areas.

An important advantage of the system of the present invention is that leaking valves can be tolerated since any leak from a closed valve will be vented through the second purge line. It will therefore not reach the connecting line since there is a net reverse flow through the outlet line. This effectively extends the usefulness of the valve before replacement. When the time comes to select another sample, the previously selected one is first closed and the desired one is then open. Any type of gas or liquid may be sampled as long as they are compatible with the hardware like tubing, valves, etc.

Of course various modifications could be made to the embodiments above without departing from the scope of the invention as defined in the appended claims.

What is claimed is:

1. A fluid sampling system for providing a fluid sample to a fluid processing apparatus, said sampling system comprising:
    a sample outlet to be connected to the input of the fluid processing apparatus;
    a plurality of sampling channels, each of said sampling channels comprising:
        an inlet line receiving a fluid and an outlet line conveying said fluid to said sample outlet;
        a valve connected to said inlet line and to said outlet line, said valve having a closed position preventing a fluid flow between said inlet line and said outlet line and an open position allowing a fluid flow between said inlet line and said outlet line;
        a first purge line connected to said inlet line for purging fluid therefrom, and a second purge line connected to said outlet line for purging fluid therefrom; and
        flow controlling means for controlling a fluid flow in each of said first and second purge lines; said fluid sampling system further comprising:
    a connecting line for connecting said outlet lines of said plurality of sampling channels to each other and to said sample outlet; and
    valve control means for selectively setting the valve of one of said sampling channels in the opened position to permit fluid to flow from said inlet line to said outlet line of said one sampling channel and the valves of the remaining sampling channels in the closed position.

2. A fluid sampling system according to claim 1, wherein said flow control means of each sampling channel comprises a first and a second rotometer respectively connected to said first and second purge lines of said each sampling channel.

3. A fluid sampling system according to claim 1, wherein said connecting line comprises a first line segment connected to said outlet line of each of said plurality of sampling channels and a second line segment having one end connected to said first line segment and another end connected to said sample outlet.

4. A fluid sampling system according to claim 3, wherein said first line segment of said connecting line forms a closed loop.

5. A fluid sampling system according to claim 3, further comprising a backpressure regulator connected to said second line segment.

6. A fluid sampling system according to claim 1, said second purge line of each sampling channel is connected to said outlet line of said each sampling channel through said valve of said each sampling channel, so that said second purge line of said each sampling channel is adapted to purge dead volume from said valve of said each sampling channel.

7. A fluid sampling system according to claim 6, wherein each said valve of said each sampling channel comprises:
    an inlet conduit connected to said inlet line of said each sampling channel for receiving fluid therefrom;
    an outlet conduit connected to said outlet line of said each sampling channel and to said inlet conduit of said each sampling channel, for conveying fluid to said outlet line of said each sampling channel;
    a purge conduit connected to said second purge line of said each sampling and to said outlet conduit of said each sampling channel; and
    a plunger translationally mounted in said purge conduit of said each sampling channel, said plunger selectively allowing or blocking a flow of fluid between said inlet and outlet conduits of said each sampling channel, thereby defining said opened and closed position of the valve of said each sampling channel.

8. A fluid sampling system according to claim 7, wherein said plunger of said each sampling channel is shaped to allow a fluid flow in said purge conduit of said each sampling channel towards said second purge line of said each sampling channel when said valve of said each sampling channel is in either of the opened and closed positions.

9. A fluid sampling system according to claim 1, wherein said valve control means of each said sampling channel comprises a manual actuator provided on each of said valves.

10. A fluid sampling system according to claim 1, wherein said valve control means comprises an electrical actuator.

* * * * *